United States Patent [19]

Roser et al.

[11] Patent Number: 5,621,094

[45] Date of Patent: Apr. 15, 1997

[54] METHOD OF PRESERVING AGAROSE GEL STRUCTURE DURING DEHYDRATION BY ADDING A NON-REDUCING GLYCOSIDE OF A STRAIGHT-CHAIN SUGAR ALCOHOL

[75] Inventors: Bruce J. Roser, Balsham; Camilo Colaco, Trumpington, both of England

[73] Assignee: Quadrant Holdings Cambridge Limited, Cambridge, England

[21] Appl. No.: 255,565

[22] Filed: Jun. 8, 1994

Related U.S. Application Data

[63] Continuation of Ser. No. 965,384, filed as PCT/GB91/00759, May 14, 1991, abandoned.

[30] Foreign Application Priority Data

May 14, 1990 [GB] United Kingdom .................. 9010742

[51] Int. Cl.⁶ .............................. C12Q 1/68; C07G 3/00; C07G 17/00; C07H 15/04
[52] U.S. Cl. .............................. 536/114; 435/6; 536/4.1; 536/120
[58] Field of Search ........................ 536/114, 4.1, 120; 435/6

[56] References Cited

U.S. PATENT DOCUMENTS

| | | | |
|---|---|---|---|
| 3,557,717 | 1/1971 | Chivers | 107/54 |
| 3,619,294 | 11/1971 | Black et al. | 127/30 |
| 3,632,357 | 1/1972 | Childs | 99/134 R |
| 3,655,442 | 4/1972 | Schwer et al. | 127/58 |
| 4,127,502 | 11/1978 | Li Mutti et al. | 252/408 |
| 4,158,544 | 6/1979 | Louderback | 23/230 B |
| 4,209,372 | 6/1980 | Bluestein et al. | 204/180 G |
| 4,327,076 | 4/1982 | Puglia et al. | 424/38 |
| 4,327,077 | 4/1982 | Pugila et al. | 424/38 |
| 4,588,744 | 5/1986 | McHugh | 514/470 |
| 4,701,417 | 10/1987 | Portenhauser et al. | 436/13 |
| 4,737,533 | 4/1988 | Charmot et al. | 524/22 |
| 4,762,857 | 8/1988 | Bollin, Jr. et al. | 514/777 |
| 4,826,825 | 5/1989 | Mitsuhashi et al. | 514/53 |
| 4,865,871 | 9/1989 | Livesey et al. | 427/4 |
| 4,883,762 | 11/1989 | Hoskins | 436/18 |
| 4,891,319 | 1/1990 | Roser | 435/188 |
| 5,009,900 | 4/1991 | Levine et al. | 426/96 |
| 5,098,893 | 3/1992 | Franks et al. | 514/54 |
| 5,290,765 | 3/1994 | Wettlaufer et al. | 514/23 |
| 5,348,852 | 9/1994 | Bonderman | 435/4 |
| 5,422,384 | 6/1995 | Samuels et al. | 523/170 |

FOREIGN PATENT DOCUMENTS

| | | |
|---|---|---|
| 0415567 | 3/1991 | European Pat. Off. . |
| 7773 | 3/1970 | France . |
| 4-297405 | 10/1992 | Japan . |
| 2206273 | 1/1989 | United Kingdom . |
| WO87/00196 | 1/1987 | WIPO . |
| WO89/06542 | 7/1989 | WIPO . |
| WO92/02133 | 2/1992 | WIPO . |
| WO90/05182 | 5/1992 | WIPO . |
| WO95/33488 | 12/1995 | WIPO . |

OTHER PUBLICATIONS

Chemical Abstracts, vol. 110, 1989, (Columbus, Ohio, US), K. Gekko, et al.: "Amino acid solubility and protein stability in aqueous maltito solutions" abstract 110409n, & Agric. Biol. Chem. 1989, 53(1), 89–95.

Japanese Patents Gazette, week 8538, 1985, No. J60149–972A (Iatron Laboratories), abstract.

Japanese Patents Gazette, week 8825, 1988, No. J63106–562A (Green Cross), abstract.

Patent Abstracts of Japan, C–Field, 17 Apr. 1987, & JP, A, 61260882 (Wakamoto Pharmaceut Co. Ltd.) 19 Nov. 1986.

Patent Abstracts of Japan, 13 Nov. 1986, & JP, A, 61139384 (Nippon Shinyaku Co. Ltd.) 26 Jun. 1986.

Chemical Abstracts, vol. 95, 1981, (Columbus, Ohio, US), Ooizumi Tooru et al.: "Quantitative aspect for protective effect of sugar and sugar alcohol against denaturation of fish myofibrils".

Japanese Patent Gazette, week 8825, 1988, No.J63106–252A (Green Cross), Abstract.

Goodrich et al., "Preservation of metabolic activity in lyophilized human erthyrocytes" *Proc. Natl. Acad. Sci. USA* (1992) 89:967–971.

Jeyendran et al., "Fertility of dehydrated bull semen" *Cryobiology* (1981) 18:292–300.

Mazur, "Cryobiology: The freezing of biological systems" *Science* (1970) 168:939–949.

*Primary Examiner*—David M. Naff
*Assistant Examiner*—S. Saucier
*Attorney, Agent, or Firm*—Morrison & Foerster

[57] ABSTRACT

A method of preserving delicate biological substances or organic compounds (a) in a dry state and/or (b) at elevated temperatures and/or (c) under irradiation comprises incorporating in a system containing the said substances or compounds, a sugar or a sugar derivative selected from (i) a non-reducing glycoside of a polyhydroxy compound selected from sugar alcohols and other straight chain polyalcohols, or (ii) a non-reducing oligosaccharide selected from raffinose, stachyose and melezitose. In particular, methods for preserving dehydrated agarose gels comprising adding lactitol or glucopyranosyl-mannitol or glucopyranosyl-sorbitol to the gel during formation and prior to dehydration are disclosed.

11 Claims, No Drawings

METHOD OF PRESERVING AGAROSE GEL STRUCTURE DURING DEHYDRATION BY ADDING A NON-REDUCING GLYCOSIDE OF A STRAIGHT-CHAIN SUGAR ALCOHOL

This application is a continuation of U.S. application Ser. No. 07/965,384, filed as PCT/GB91/00759, May 14, 1991, now abandoned.

This invention relates to the stabilization of biological macromolecular substances, in particular proteins and the like, such as enzymes, antibodies, fluorescent agents, vaccines etc., under dry and/or hot and/or irradiated conditions.

Our earlier patent (GB 2,187.171, U.S. Pat. No. 4,891,319) and applications (PCT/GB89/00047, PCT/GB89/00093) disclosed and claimed the use of the non-reducing sugar trehalose to preserve biological compounds while being dried at ambient temperature. An additional advantage of that process is that the compounds are not only stabilized during the drying procedure, but are also stabilized against long-term storage at relatively high ambient temperatures. Our earlier application (EP-A-0415567) diclosed the stabilisation also of low-molecular weight compounds such as antibiotics, chelating agents and nucleosides. Other compounds needing protection include vitamins.

Trehalose is a highly effective agent for this purpose and, in our subsequent research, has effectively provided a standard against which any other stabilizing agent must be compared. However, suitably pure trehalose is not readily available in large quantities. There is therefore a need for alternative stabilizing agents. Sugars in general are of limited use. For most purposes reducing sugars do not provide the degree of stabilization required, especially during the drying procedure at a relatively high ambient temperature. Furthermore, reducing sugars are found to be of very little help in long-term stabilization and, in some cases can be highly deleterious. Other apparently non-reducing sugars, such as sucrose, again have limited utility and, even if they provide good stabilization during the drying step, they again provide very inferior long-term stabilization.

A chance observation that, under unusual circumstances, trehalose will crystallize on drying and that biological materials associated with the crystalline trehalose lacked protection, led to a search for compounds which could be dried without crystallizing, which were non-reducing but which were polyhydroxy compounds capable of replicating the effect of trehalose. We have now found that one particular type of carbohydrate material fulfills these requirements and is extremely effective in stabilizing biological materials both during the drying step and for long term storage.

The compounds in question are non-reducing glycosides of polyhydroxy compounds selected from sugar alcohols and other straight chain polyalcohols. Other useful compounds include raffinose, stachyose and melezitose.

The sugar alcohol glycosides are preferably monoglycosides, in particular the compounds obtained by reduction of disaccharides such as lactose and maltose. The glycosidic group is preferably a glucoside or a galactoside and the sugar alcohol is preferably sorbitol (glucitol).

Particularly preferred compounds are maltitol (4-O-β-D-glucopyranosyl-D-glucitol), lactitol (4-O-β-D-galactopyranosyl-D-glucitol) and the two isomers of palatinit, the sugar alcohol derived from isomaltulose (palatinose) (6-α-D-glucopyranosyl-mannitol and 6-α-D-glucopyranosyl-sorbitol).

In comparative tests we have shown that these compounds are surprisingly very effective in contrast to other sugar alcohols and other sugars, whether reducing or not.

An example of the beneficial effect of the compounds according to this invention is as follows:

Molecular biology techiques which form the basis for the technology of genetic engineering depend on the use of highly specific reagents. An important class of such reagents are the so called restriction enzymes. These proteins, largely derived from bacterial sources, have the property of recognising particular sequences of nucleotides in the DNA chain where they cause scission of the inter nucleotide bonds and cut the DNA into precise and reproducible fragments. These enzymes vary considerably in stability. Some are stable even at elevated temperature while others are among the most fragile biological reagents known. As a consequence, these enzymes are difficult and expensive to store, ship and handle. Routinely, these reagents are shipped in small aliquots of a few micrograms packed in solid $CO_2$ in large foam-polystyrene containers and transported by express services usually by air. This adds considerably to their cost. On receipt they are aliquoted and stored at −20° C. Even at −20° C. some have a relatively brief shelf life and need to be replaced after a few months. A technique which would enable such enzymes and other molecular biology reagents to be transported and stored at room temperature or above with a long shelf life would be of considerable value.

We have found that all restriction enzymes, even the most unstable, can be dried without loss of activity. In the dried form these preparations show very surprising stability and can be kept at up to +55° C. for prolonged periods with no detectable loss of activity.

Other sugars and sugar derivatives in contrast have no preservative effect on the stability of these enzymes. Drying in the presence of effective preservatives such as lactitol enables entirely new techniques for using restriction enzymes to be developed. In one such process, the enzymes are dried in the plastic wells of multi-well format microtitration plate (e.g. one with 96 wells). For use, the DNA to be cut is added to the dry well containing the appropriate enzyme in dried form. The water in which the DNA is dissolved, acts as a solvent for the dried enzymes which immediately regain full activity and cut the DNA in a manner identical with the activity of fresh enzyme. This simple one step process should be compared with existing techniques which require that frozen tubes of enzyme be removed from the freezer, aliquoted on ice, diluted in special buffers, added to fresh tubes to which the DNA is subsequently added and then incubated; a more labour intensive operation. For certain applications such as Restriction Fragment Length Polymorphism (RFLP) analysis, a collection of several enzymes is used to cut the same DNA and the pattern of fragments produced by each enzyme is analysed by gel electrophoresis. This technique can be greatly simplified by drying the requisite panel of enzymes in rows of 96 well plates. Thus up to 8 rows of 12 enzymes (or 12 rows of 8 enzymes) can be stored in a single plate. In use, multiple tip pipettes are used to add DNA simultaneously to a whole row of enzymes and all the digests are performed simultaneously with only one manoeuvre.

Dried plates of this type are conveniently stored on a laboratory shelf and do not require either freezing or refrigeration. They are entirely stable for very prolonged periods. Accelerated ageing tests indicate a shelf life of at least 12 months at room temperature. It is probable that the life span is essentially indefinite.

Remarkably, certain sugars which have been claimed by others to have a preservative function are not useful and in some cases positively harmful to the preservation of the biological function of proteins. Thus lactose, and especially palatinose, accelerate the irreversible photobleaching of R-phycoerythrin in solution and completely fail to preserve the activity of restriction enzymes. Sucrose preserves the biological activity of restriction enzymes immediately after drying, but on storage at 37° C. progressive damage occurs to the enzymes and after 5 weeks at this temperature, all activity is lost. In contrast trehalose, the disaccharide sugar alcohols lactitol (galactopyranosyl-sorbitol), glucopyranosyl mannitol and glucopyranosyl sorbitol give good preservation of activity. With these sugar alcohols this stabilizing effect is apparently indefinite at elevated temperatures. This is also true of the non-reducing higher sugars such as the trisaccharides raffinose and melezitose. The reducing trisaccharide maltotriose shows no preservative activity on storage at 37° C. for 2 weeks. The non-reducing tetrasaccharide stachyose is a good preservative.

In essence, the ability of added carbohydrate to preserve protein stability at elevated temperatures (ambient and above) correlates completely with the absence of a reducing function in the carbohydrate. This can however be an indirect function of the stability of the disaccharide bond. Thus sucrose is a good stabilizing agent short term but within a few weeks at 37° C. the protein is destroyed, presumably because of chemical breakdown of the glycosidic bond in sucrose (one of the highest bond energies in biochemistry) which causes secondary chemical damage to the macromolecules.

Absence of a reducing group is not sufficient to guarantee stabilizing ability. Thus the monosaccharide sugar alcohols galactitol, mannitol and erythritol are not satisfactory protective agents. This is not due to the fact that a ring structure is required for stabilizing activity. Sorbitol (glucitol), a straight chain non-reducing monosaccharide alcohol, does have some limited activity as a stabilizing agent while myo-inositol, a non-reducing 6 carbon ring compound is without stabilizing activity.

Of particular importance is the observation that the compounds which stabilize proteins during drying also protect proteins against free radical damage in solution. While we do not wish to be bound by theory, we speculate that this effect is not due to the molecules acting as free radical scavengers because the effective compounds are chemically the most non-reactive and therefore most unlikely to compete for free-radical interaction. It seems more likely that these carbohydrate molecules are able to bind to proteins in solution and act as a buffer between the protein and free radicals produced in the surrounding solvent. Being much larger than water molecules and therefore posessing a much higher moment of inertia, it seems likely that the short lived free radicals cannot displace hydrogen bonded sugar molecules (and damage the protein) within their short life-times. The disaccharide palatinose (isomaltulose) is actively destructive in this test thus showing that single examples of a stabilizing effect of a particular sugar are valueless in predicting its usefulness as a protective agent for biological molecules.

We also believe that the ability of effector molecules to coat proteins and other biological molecules with an amorphous phase of hydrogen-bonded carbohydrate is an important element in their protective effect. This is exemplified by experiments in which the fluorescent protein phycoerythrin was dried from 0.6M trehalose solution under conditions in which part of the solidifying mixture crystallised and part solidified as an amorphous glass. Only in the latter phase was the fluorescence of RP-E preserved. Similar data was obtained in drying agarose gels. Where trehalose was used as a preservative, excellent preservation of the agarose structure, as shown by the ability of the dried gel to rehydrate to its original volume, was obtained where amorphous glass transformation occured. If the trehalose crystallised during drying, the agarose structure was not preserved and the gels in the area in which crystals formed did not reconstitute on addition of water. When agarose gels were dried in the presence of a sugar derivative which always formed an amorphous glass, such as lactitol, the gels showed uniform and complete preservation of structure and function.

The preservative properties of the non-reducing oligosaccharides and oligosaccharide alcohols were not confined to air drying or high temperature storage, nor to the preservation of proteins and carbohydrates. Lyophilised materials also showed excellent protective effects of the same carbohydrates as detailed above. In addition, lipids, especially lipids dispersed as emulsions or liposomes in aqueous buffers could be dried from the same carbohydrate solutions with complete preservation of their properties.

According to the present invention, we thus provide a method of stabilizing delicate biological materials such as proteins, lipids, antibodies etc. for long-term storage under dry conditions, by drying a mutual solution of the biological material and a stabilizing carbohydrate selected from non-reducing sugar alcohol glycosides and non-reducing oligosaccharides having at least three saccharide groups.

We also provide stabilized biological substances formed by drying a solution of the substance in the presence of one of said stabilizing carbohydrates. The invention can thus be seen as having the same applicability as our earlier trehalose process.

We also provide stabilized solutions/suspensions in water.

The following Examples illustrate the invention.

EXAMPLE 1

The typical restriction endonuclease Pst I is commonly used for molecular cloning and gives a very characteristic pattern of phage lambda DNA fragment lengths in electrophoresis gels.

The enzyme was diluted in sterile 96-well U-bottomed polystyrene or PVC plastic plates. These were air dried in a laminer flow hood for 12–16 hours at room temperature (about 18°–25° C.) and stored at room temperature, 37° C. or 55° C. for different periods of time for accelerated ageing studies. The drying mixture consisted of three units of the enzyme in 0.45 or 0.6M trehalose or other sugar or sugar derivative in the presence of a proprietary buffer at 10 μl/well. The single buffer enabled cutting of DNA with all restriction enzymes and contained a molecular "water pump" component (see PCT/GB89/00093).

Buffer: 33mM Tris acetate buffer (pH7.4)

66mM Sodium acetate 1 mM Magnesium acetate 1 mM Dithiotreitol 3 mM Spermidine 0.1 mg/ml Bovine Plasma Albumin Results The activity of fresh and dried enzyme was determined by assaying their ability to produce the characteristic pattern of bands from 0.3 μg of lambda bacteriophage DNA digested at 37° C. for 30 mins and separated by electrophoresis on 1% agarose gels. Enzymes showed no loss of activity after 10 weeks at 55° C. To confirm full retention of enzymatic activity one experiment was also done in which limiting amounts of enzymes were titrated out from 5 units to 0.5 units per well and used to cut 0.3 μg lambda DNA. Trehalose-dried titrated enzymes were compared with titrations of fresh enzymes. After storage for 2 weeks at 37° C. the enzyme titred identically to fresh enzyme showing no loss of activity on drying and storage.

Since it is well known that long term damage to macromolecules dried in sugars can result from chemical attack on the macromolecule by the reducing groups in certain mono and disaccharides, these experiments were repeated with several alternative sugars and their non reducing alcohol derivatives. Pst I was dried as above and also in buffers containing a large number of other sugars and chemical derivatives of common sugars. Trehalose again showed 100% preservation (Table 1a and b).

TABLE 1a

Storage of dried Pst I in Different Carbohydrates

| CARBOHYDRATE | CHEMICAL NAME | RED | TEMP | TIME | PRESERVATION |
|---|---|---|---|---|---|
| Glucose | α-D-glucopyranose | + | 37° | 1 | + |
| | | | " | 14 | − |
| Galactose | α-D-galactopyranose | + | " | 1 | − |
| Mannose | α-D-mannopyranose | + | " | 1 | − |
| Sorbitol | D-glucitol | − | " | 1 | ++ |
| | | | " | 14 | + |
| | | | " | 70 | − |
| Galactitol | 6 carbon alcohol | − | " | 1 | − |
| Mannitol | " | − | " | 1 | − |
| Erythritol | 4 carbon alcohol | − | " | 14 | − |
| Myo-Inositol | (1α,2α,3α,4β,5α,6β)cyclo-hexanehexol | − | " | 14 | − |
| Threitol | 4 carbon alcohol | − | " | 14 | − |
| Trehalose | α-D-glucopyranosyl-α-D-glucopyranoside | − | " | 14 | +++ |
| | | | " | 70 | +++ |
| | | | 55° | 70 | +++ |
| Sucrose | β-D-fructofuranosyl-α-D-glucopyranoside | − | 37° | 14 | ++± |
| | | | " | 35 | − |
| Maltose | 4-O-α-D-glucopyranosyl-D-glucose | + | " | 14 | − |
| Lactose | 4-O-β-D-galactopyranosyl-glucopyranose | + | " | 14 | − |
| Palatinose | α-D-glucopranosyl-1,6-fructose | + | " | 14 | − |
| Lactulose | 4-O-β-D-galactopyranosyl-D-fructose | + | " | 14 | − |
| Maltitol | 4-O-β-D-glucopyranosyl-D-glucitol | − | " | 14 | +++ |
| | | | " | 70 | +++ |
| Lactitol | 4-O-β-D-galactopyranosyl-D-glucitol | − | " | 14 | +++ |
| | | | " | 70 | +++ |
| | | | 55° | 70 | +++ |

TABLE 1b

Storage of Dried Pst I in Various Carbohydrates

| CARBOHYDRATE | CHEMICAL NAME | RED | TEMP | TIME | PRESERVATION |
|---|---|---|---|---|---|
| Palatinit | 1:1 mixture glucopyranosyl-1→6-mannitol+1,6-sorbitol | − | 37° | 14 | +++ |
| | | | | 70 | + |
| Palatinit isomer 1 | α-D-glucopyranosyl-1→6-mannitol | − | 37° | 14 | +++ |
| | | | " | 70 | + |
| Palatinit isomer 2 | α-D-glucopyranosyl-1→6-sorbitol | − | " | 14 | +++ |
| | | | " | 70 | +++ |
| Maltotriose | O-α-D-glucopyranosyl(1→4)-O-α-D-glucopyranosyl(1→4)-D-glucose | + | " | 14 | − |
| Raffinose | β-D-fructofuranosyl-O-α-D-galactopyranosyl-(1→6)-α-glucopyranoside | − | " | 14 | +++ |
| Melezitose | O-α-D-glucopyranosyl-(1→3)-β-D-fructofuranosyl-α-D-glucopyranoside | − | " | 14 | +++ |
| Stachyose | β-D-fructofuranosyl-O-α-D-D-galactopyranoayl-(1→6)-β-D-fructofuranosyl-α-D-glucopyranoside | − | " | 14 | +++ |
| Methyl glucoside | methyl-α-D-glucopyranoside | − | " | 14 | − |
| Methyl mannoside | methyl-α-D-mannopyranoside | − | " | 14 | − |
| Lactulose | | + | " | 14 | + |
| | | | | 35 | − |

RED = reducing sugar

Neither palatinose nor lactose preserved any enzymatic activity. When lactitol was substituted for palatinose or lactose, activity was preserved at all temperatures in a manner equivalent to trehalose i.e. all enzymes were fully active after 10 weeks at 55° C.

Sugar alcohols of the reducing disaccharides gave much better results than the parent disaccharide suggesting that complete lack of-reducing activity plus lower-energy glycosidic linkages which resist chemical attack are an important feature of trehalose and other potential preservatives. Interestingly, sugar alcohols of the monosaccharides were poor preservatives except for sorbitol which was only modestly effective.. With the higher sugars, again only the non-reducing trisaccharides and the non-reducing tetrasaccharide stachyosewere effective.

EXAMPLE 2

The fluorescent phycobiliprotein R-phycoerythrin is a 240 KD protein extracted from red algae. It has a fluorescence efficiency of 0.98 and emits orange-red light when illuminated with 490 run blue light. The molecule is very susceptible to desiccation damage and cannot even be lyophilised without collapse of molecular structure and loss of fluorescence. R-PE is also denatured in solution by excitation light in the UV-Blue band of the spectrum. This denaturation is mediated by-free radicals created in the solvent water by the irradiation. Free radical damage is also reduced in a dose dependent manner by added trehalose and certain other sugars and sugar alcohols but is, unexpectedly, greatly accelerated by other sugars such as palatinose (Table II)

TABLE II

| Carbohydrate | % loss of fluorescence of R-PE solutions | |
| --- | --- | --- |
|  | 5 min | 20 min |
| trehalose | 9% | 48% |
| isomaltulose | 93% | 100% |
| lactitol | 13% | 47% |
| glucopyranosyl-mannitol (GPM) | 21% | 47% |
| glucopyranosyl-sorbitol (GPS) | 7% | 43% |
| nil | 17% | 55% |

From these results it will be seen that while the two reduced forms of isomaltulose are effective in reducing the loss of fluorescence, isomaltulose itself exhibited a disastrous effect on the fluorescence.

The same panel of sugars and derivatives was used to dry and store a variety of other biological molecules at various temperatures, with essentially similar results.

EXAMPLE 3

An immunoconjugate produced by covalent bonding of the F(ab)$_2$ fragment of rabbit antibodies against rat immunoglobulin to peroxidase obtained from horseradish.

The conjugate was dried in various sugars and alcohols at a concentration of 15 migrogram per ml and 10% sugar by weight and stored for 2 or 4 weeks at 37° or 55° C. and titrated for its activity on plates coated with a rat monoclonal antibody.

In trehalose no activity was lost at all. The average values for other sugars and alcohols at 4 weeks were:

| GPM = | 86%; | maltitol | 67%; | maltose | 49% |
| --- | --- | --- | --- | --- | --- |
| lactitol = | 86%; | palatinit | 68%; | GPS | 57% |
| glucose = | 12%; | no sugar | 0%; | | |

EXAMPLE 4

Agarose gels 7.5 cm×10 cm×0.6 cm were poured from molten agarose (1% w/v) containing 15% by weight of various sugars. The gels were dried and stored at various temperatures. When rehydrated, the % regain of gel volume was measured and the gels were used in electrophotosis to separate the Hind III fragments of phage Lambda DNA as a check on function.

RESULTS

All gels failed to rehydrate and to separate DNA after storage at 55° C. which seems to be above the re-melting temperature of agarose. At 37° C. lactitol and trehalose were perfect from >12 weeks. Also perfect were GPs and GPM. Palatinose failed after 2 weeks, glucose, mannitol and sorbitol failed after 1 week.

We claim:

1. A method of preserving dehydrated agarose gel structure comprising dehydrating a hydrated agarose gel formed from a mixture comprising agarose and an amount of a non-reducing glycoside of a straight chain sugar alcohol sufficient to maintain gel structure upon dehydration wherein the non-reducing glycoside of a straight chain sugar alcohol does not form crystals during dehydration and wherein the agarose gel retains its structure upon rehydration.

2. The method according to claim 1 wherein the non-reducing glycoside of a polyhydroxy straight chain sugar alcohol is lactitol.

3. The method according to claim 1 wherein the hydrated gel comprises about 1% agarose and about 15% lactitol.

4. A method of preserving dehydrated agarose gel structure comprising dehydrating a hydrated agarose gel containing an amount of lactitol sufficient to maintain gel structure upon dehydration, wherein the lactitol does not form crystals during dehydrating and wherein the agarose gel retains its structure upon rehydration.

5. The method according to claim 4 wherein the hydrated gel comprises about 1% agarose and about 15% lactitol.

6. A composition comprising a dehydrated agarose gel comprising agarose and a non-reducing glycoside of a straight chain sugar alcohol, sufficient to maintain gel structure upon dehydration wherein the non-reducing glycoside of a straight chain sugar alcohol does not form crystals during dehydration and wherein the agarose gel retains its structure upon rehydration.

7. The composition according to claim 6 wherein the non-reducing glycoside of a straight chain sugar alcohol is lactitol.

8. The composition according to claim 6 wherein upon hydration, the gel comprises about 1% agarose and about 15% of the non-reducing glycoside of a straight chain sugar alcohol.

9. The composition according to claim 8 wherein the the non-reducing glycoside of a straight chain sugar alcohol is lactitol.

10. A composition comprising a dehydrated agarose gel for subsequent use in a hydrated form comprising agarose and lactitol an amount sufficient to maintain gel structure upon dehydration, wherein the agarose gel retains its structure upon rehydration.

11. The composition according to claim 10 wherein the rehydrated gel comprises about 1% agarose and 15% lactitol.

* * * * *